(12) United States Patent
Grandt

(10) Patent No.: US 9,717,615 B2
(45) Date of Patent: Aug. 1, 2017

(54) DOUBLE LAYERED BALLOONS IN MEDICAL DEVICES

(75) Inventor: Axel Grandt, Strassberg (DE)

(73) Assignee: ABBOTT LABORATORIES VASCULAR ENTERPRISES, Dublin (IE)

(*) Notice: Subject to any disclaimer, the term of this patent is extended or adjusted under 35 U.S.C. 154(b) by 1347 days.

(21) Appl. No.: 12/809,061

(22) PCT Filed: Dec. 19, 2008

(86) PCT No.: PCT/EP2008/010946
§ 371 (c)(1),
(2), (4) Date: Sep. 28, 2010

(87) PCT Pub. No.: WO2009/080320
PCT Pub. Date: Jul. 2, 2009

(65) Prior Publication Data
US 2011/0022152 A1    Jan. 27, 2011

(30) Foreign Application Priority Data
Dec. 21, 2007 (EP) .................................... 07025021

(51) Int. Cl.
*A61F 2/06* (2013.01)
*A61F 2/958* (2013.01)
*A61M 25/10* (2013.01)

(52) U.S. Cl.
CPC ...... *A61F 2/958* (2013.01); *A61F 2002/9583* (2013.01); *A61M 25/1029* (2013.01)

(58) Field of Classification Search
CPC ...... A61M 2025/1075; A61M 25/1029; A61M 2025/1031; A61M 25/1027;
(Continued)

(56) References Cited

U.S. PATENT DOCUMENTS 3,045,677 A * 7/1962 Wallace ............. A61M 25/1011
604/101.05
4,896,669 A * 1/1990 Bhate ................ A61M 25/1006
604/103.1
(Continued)

FOREIGN PATENT DOCUMENTS

EP    0669143    8/1995
EP    0778012    6/1997
(Continued)

OTHER PUBLICATIONS

U.S. Appl. No. 12/809,059, Jan. 30, 2014, Office Action.

*Primary Examiner* — Melanie Tyson
*Assistant Examiner* — Erin Colello
(74) *Attorney, Agent, or Firm* — Baker Botts L.L.P.

(57) ABSTRACT

The present invention refers to medical devices. Particularly it relates to stent devices and balloon catheter devices. In the most particular aspect of the invention it relates to balloon catheter devices carrying stents (2) with the medical balloon (3) comprising an inner layer (4) having a lower compliance rate and/or burst pressure than the outer layer (5) and an outer layer (5) having on the outer surface (6a) a higher adhesion strength than the inner layer (4), and its use in a variety of medical procedures to treat medical conditions in animal and human patients.

15 Claims, 4 Drawing Sheets

(58) Field of Classification Search
CPC .... A61M 2025/1059; A61F 2002/9583; A61F 2250/0019; A61F 2002/9505; A61F 2002/9522; A61F 2/958; A61F 2/95; A61F 2002/9586; A61F 2002/9665
See application file for complete search history.

(56) References Cited

U.S. PATENT DOCUMENTS

| | | | | |
|---|---|---|---|---|
| 5,002,531 A * | 3/1991 | Bonzel | ............. | A61M 25/0032 604/913 |
| 5,250,070 A * | 10/1993 | Parodi | ................. | A61M 25/104 604/103.08 |
| 5,304,135 A * | 4/1994 | Shonk | ...................... | 604/103.11 |
| 5,342,305 A * | 8/1994 | Shonk | ................. | A61M 25/104 604/101.02 |
| 5,477,856 A * | 12/1995 | Lundquist | ..................... | 600/373 |
| 5,556,383 A | 9/1996 | Wang et al. | | |
| 5,693,014 A * | 12/1997 | Abele et al. | ............. | 604/103.08 |
| 5,704,913 A * | 1/1998 | Abele | ................. | A61M 25/1011 604/101.02 |
| 5,769,817 A | 6/1998 | Burgmeier | | |
| 5,797,948 A * | 8/1998 | Dunham | ................ | A61M 25/10 600/3 |
| 5,810,767 A * | 9/1998 | Klein | ....................... | A61B 8/12 604/103.01 |
| 5,830,182 A | 11/1998 | Wang et al. | | |
| 5,833,657 A * | 11/1998 | Reinhardt et al. | ........ | 604/101.02 |
| 5,843,116 A * | 12/1998 | Crocker | ............ | A61M 25/1002 604/103.07 |
| 5,893,868 A | 4/1999 | Hanson et al. | | |
| 5,935,135 A * | 8/1999 | Bramfitt | .................. | A61F 2/958 606/191 |
| 5,954,740 A * | 9/1999 | Ravenscroft | ...... | A61M 25/1002 604/103.07 |
| 5,957,930 A | 9/1999 | Vrba | | |
| 5,976,181 A * | 11/1999 | Whelan | ................... | A61F 2/958 606/194 |
| 6,024,753 A | 2/2000 | Claren et al. | | |
| 6,033,433 A | 3/2000 | Ehr et al. | | |
| 6,036,697 A | 3/2000 | DiCaprio | | |
| 6,048,332 A * | 4/2000 | Duffy | ................ | A61M 25/1002 604/103.01 |
| 6,068,608 A * | 5/2000 | Davis | ................. | A61M 25/1011 604/4.01 |
| 6,171,278 B1 | 1/2001 | Wang et al. | | |
| 6,203,558 B1 * | 3/2001 | Dusbabek | ................ | A61F 2/958 606/108 |
| 6,306,144 B1 | 10/2001 | Sydney et al. | | |
| 6,406,457 B1 | 6/2002 | Wang et al. | | |
| 6,533,809 B2 | 3/2003 | Von Oepen | | |
| 6,544,221 B1 * | 4/2003 | Kokish et al. | ............ | 604/103.01 |
| 6,544,223 B1 * | 4/2003 | Kokish | ................. | A61L 29/085 427/2.1 |
| 6,554,841 B1 * | 4/2003 | Yang | ............................. | 606/108 |
| 6,602,285 B1 | 8/2003 | Von Oepen et al. | | |
| 6,635,078 B1 | 10/2003 | Zhong et al. | | |
| 6,695,809 B1 * | 2/2004 | Lee | ............................. | 604/96.01 |
| 6,945,957 B2 * | 9/2005 | Freyman | ............ | A61M 25/007 604/96.01 |
| 6,989,025 B2 * | 1/2006 | Burgmeier et al. | ........... | 623/1.11 |
| 7,004,963 B2 * | 2/2006 | Wang | ..................... | A61F 2/958 606/192 |
| 7,309,324 B2 * | 12/2007 | Hayes et al. | ............... | 604/96.01 |
| 7,341,571 B1 * | 3/2008 | Harris et al. | ............... | 604/96.01 |
| 7,367,989 B2 * | 5/2008 | Eidenschink | ................. | 623/1.11 |
| 7,481,799 B2 * | 1/2009 | Hehrlein et al. | .............. | 604/264 |
| 7,572,245 B2 * | 8/2009 | Herweck | ................. | A61L 29/16 604/103.02 |
| 8,034,022 B2 * | 10/2011 | Boatman | .................... | 604/96.01 |
| 8,046,897 B2 * | 11/2011 | Wang | ..................... | A61F 2/958 29/505 |
| 8,092,508 B2 * | 1/2012 | Leynov et al. | .............. | 623/1.11 |
| 8,123,793 B2 * | 2/2012 | Roach | ..................... | A61F 2/958 604/509 |
| 2002/0165523 A1 * | 11/2002 | Chin et al. | .................... | 604/523 |
| 2003/0032999 A1 * | 2/2003 | Huang | .................... | A61F 2/958 623/1.11 |
| 2004/0133263 A1 * | 7/2004 | Dusbabek et al. | ........... | 623/1.11 |
| 2004/0172119 A1 * | 9/2004 | Eidenschink | ........... | A61F 2/954 623/1.11 |
| 2004/0172121 A1 * | 9/2004 | Eidenschink et al. | ....... | 623/1.11 |
| 2006/0136032 A1 | 6/2006 | Legarda et al. | | |
| 2007/0016278 A1 * | 1/2007 | Shippy et al. | ............... | 623/1.11 |
| 2007/0106216 A1 * | 5/2007 | Noddin | ............ | A61M 25/1029 604/103.09 |
| 2007/0142771 A1 * | 6/2007 | Durcan | .................... | 604/103.06 |
| 2007/0208365 A1 | 9/2007 | Lee et al. | | |
| 2007/0267128 A1 | 11/2007 | Horn et al. | | |
| 2009/0254064 A1 * | 10/2009 | Boatman | ....................... | 604/509 |
| 2011/0046711 A1 | 2/2011 | Degen et al. | | |

FOREIGN PATENT DOCUMENTS

| | | |
|---|---|---|
| EP | 0903161 | 3/1999 |
| WO | WO 96/04951 | 2/1996 |
| WO | WO 00/57815 | 10/2000 |
| WO | WO 2005/009526 | 2/2005 |
| WO | WO 2005/025648 | 3/2005 |
| WO | WO 2007/120323 | 10/2007 |
| WO | WO 2009/080320 | 7/2009 |
| WO | WO 2009/080322 | 7/2009 |

* cited by examiner

A

B

DOUBLE LAYERED BALLOONS IN MEDICAL DEVICES

CROSS-REFERENCE TO RELATED APPLICATIONS

This application is a U.S. Nationalization of PCT Application Number PCT/EP2008/010946 filed 19 Dec. 2008, entitled "DOUBLE LAYERED BALLOONS IN MEDICAL DEVICES," which claims the benefit of and priority to European Patent Application No. 07025021.2 filed 21 Dec. 2007, entitled "DOUBLE LAYERED BALLOONS IN MEDICAL DEVICES," the entireties of which are incorporated herein by reference.

FIELD OF THE INVENTION

The present invention refers to medical devices. Particularly, it relates to stent devices and balloon catheter devices. In the most particular aspect of the invention, it relates to balloon catheter devices carrying stents with the medical balloon comprising an inner layer having a lower compliance rate and/or a higher burst pressure and/or higher durometer than the outer layer and an outer layer having on the outer surface a higher adhesion strength than the inner layer, thus increasing the retention force to a stent mounted on a balloon, and its use in a variety of medical procedures to treat medical conditions in animal and human patients.

BACKGROUND OF THE INVENTION

This invention relates to medical devices, especially to stent carrying balloon catheters, for use in angioplasty and other procedures of vessel repair. Angioplasty is an efficient and successful method of opening stenoses in the vascular system.

In a popular form of angioplasty, a balloon catheter is advanced through the vascular system until the balloon, which is carried at the distal end of a catheter shaft, and which may carry an expandable stent, is positioned across the stenosis or damaged vessel. This movement through the vessels prior to and during positioning is a first critical step in this form of angioplasty. During movement the stent may—especially if the catheter is lubricated—slip from the balloon. To counter this, there is a constant need for improved "stent retention". By then inflating the balloon, pressure is applied to the obstruction which is moved by pressing it against the inner wall of the vessel, whereby the vessel is opened for improved flow. Due to the expansion of the balloon, the stent, which—if used—is situated on the balloon, is also expanded for aiding in repairing the vessel wall and hindering obstruction. This moment of opening-up of the folded balloon is a second critical step in this form of angioplasty. As the stent is mounted on the central, cylindrical portion of the balloon, the cones of the balloon open first when the balloon is inflated. In case the proximal balloon cone opens before the distal balloon cone there is a risk that the stent can slip off the balloon and get lost in vasculature. In case the balloon cones open symmetrically as intended and in case the frictional forces between the balloon and the stent are low, as is the case especially with smooth material like Nylon forming the balloon, there is a risk that the stent will be compressed longitudinally between the opening balloon cones thus foreshortening of the stent. Is increased. It is therefore another important need to counter this complication which is hindering a correct positioning of the stent. As a last step the stent is then released by deflating the balloon reducing its circumference until refolding of the balloon occurs followed by removal of the balloon and catheter from the vessel. In some cases the refolding is insufficient leading to deformations, like, e.g., the so called "pancake-effect", in which the refolded balloon does not reach the optimal minimum—mostly circular—size.

There are various types of balloon catheters. One type is fed over a guide wire (i.e., "over-the-wire" catheters) and another type serves as its own guide wire ("fixed-wire" catheters). There have been development variations of these two basic types: the so called "rapid exchange" type catheter, "innerless" catheters, and others. The term "balloon catheter" as defined in this invention is meant to include all the various types of angioplasty catheters which carry a balloon for performing angioplasty and any other type of stent carrying balloon catheter. Balloon catheters also have a wide variety of inner structure, such as different lumen design, of which there are at least three basic types: triple lumen, dual lumen and co-axial lumen. All these varieties of internal structure and design variations are included in the definition "balloon catheter" herein.

If a balloon catheter is used in percutaneous transluminal coronary angioplasty (PTCA), it is typically advanced through a guide catheter to a preselected vessel location, such as the aorta, for example. Using fluoroscopy, the surgeon advances the catheter until the balloon is located across the stenosis or obstruction. This may involve the use of a guide wire over which the catheter is moved or alternatively the catheter may act as its own guide wire.

The use of stents, balloons, catheters, especially balloon catheters and other medical devices etc. in minimal invasive surgery, especially in the cardiovascular field, has—over the last years—shown a high growth. As a consequence the need for modifications to the materials used fulfilling the highly specialized needs in the field of different medicinal devices has clearly risen. Especially in the field of vascular used balloons there was a clear desire for a modified material showing a suitable compliance, a high burst pressure, but also a good and dependable "stent retention" as well as reduction of "foreshortening" of the stent upon delivery.

U.S. Pat. No. 6,635,078 B1 provides a solution in which either to the inside of the stent or to the outer surface of the balloon an adhesive is applied in defined areas. Besides the first disadvantage of a further production step the adhesive usually has to be chosen well in regards to its adhesion strength to avoid further complications through hindrance of a release of the stent from the balloon after expansion or a further resistance during expansion of the balloon due to the further adhesive binding with the risk of an abrupt opening.

U.S. Pat. No. 6,306,144 B1 provides a solution in which in a certain pattern a single layer balloon catheter is lubricated in certain areas and in other areas not or less lubricated or treated with an adhesive. Besides the first disadvantage of having to adhere to very defined patterns during production either the adhesive used has to be chosen well as to avoid further complications through hindrance of release or abrupt opening. On the other hand, due to the very nature of a fluid lubricant neighboring lubricious material can easily flow into the less- or non-treated areas, even worsening the foreshortening and other slipping of the stent.

The present invention is aimed at having an improved grip or adhesion force, i.e., high friction forces between the surface of the balloon and the stent (or graft etc.) to help in better stent retention and especially avoiding the longitudinal slip of the stent during expansion of the balloon thus avoiding longitudinally compression of the stent by the increasing balloon cones and thus minimizing foreshortening of the stent during expansion, but without using an adhesive on the outer surface of the balloon nor on the inner surface of the stent. This invention thus avoids the suboptimal behavior of the known balloons during movement in the vessel and during expansion at the same time avoiding the problems associated with prior solutions.

SUMMARY OF THE INVENTION

The present invention is directed in one embodiment to a medical device, desirably a balloon catheter, comprising an expandable and contractible member, desirably a medical balloon, comprising an inner layer and an outer layer, and a second expandable medical device, desirably a stent. The inner layer is expandable and contractible through pressure provided by a gas and/or a liquid to its inner surface and desirably has a lower compliance rate and/or higher burst pressure and/higher durometer than the outer layer. Desirably, the inner layer consists of polymeric material of low compliance and high burst-pressure such as for example—and not limited to—PEBAX® of a shore hardness of more than 40D, or Nylon—like Nylon 12—or mixtures thereof. In regards to the outer layer, its outer surface does have a higher adhesion strength in contact to the second expandable medical device than the inner layer and is not formed by an adhesive. Desirably, the outer layer consists of polymeric material such as for example and not limitation to a Block-Copolymer, like PEBA® and PEBA® of a shore hardness of equal to or less than 40D. By choosing a high adhesion strength the grip or adhesion force, i.e., friction force between the surface of the balloon and the stent (or graft etc.) is improved, to help in better stent retention and especially avoiding the longitudinal slip of the stent during expansion of the balloon, thus avoiding longitudinally compression of the stent by the increasing balloon cones and thus minimizing foreshortening of the stent during expansion. On the other hand, avoiding the use of an adhesive on the outer surface of the balloon or on the inner surface of the stent does allow for a reliable and smooth stent expansion and consequent catheter removal.

In another embodiment, the invention is further directed to a medical device, desirably a balloon catheter, comprising an expandable and contractible member, desirably a medical balloon, comprising an inner layer and an outer layer, and a second expandable medical device, desirably a stent. The inner layer is expandable and contractible through pressure provided by a gas and/or a liquid to its inner surface. In regards to the outer layer, its outer surface does have a higher adhesion strength in contact to the second expandable medical device than the inner layer and is not formed by an adhesive. In addition, the outer layer is forming an uneven outer surface, either by disposing the outer layer in such a way on the inner layer that inter-spaces, hollow areas between the outer layer and the inner layer, are formed or by folding the outer layer (providing access material) in many folds so that as a result in some places a part of the outer surface of the outer layer is facing another part of the outer surface of the outer layer, so getting in contact with each other. Accordingly, by providing this rough surface resulting from the uneven distribution of the outer layer on the inner layer the grip or adhesion force between the surface of the balloon and the stent (or graft, etc.) is improved, to help in better stent retention and especially avoiding the longitudinal slip of the stent during expansion of the balloon. On the other hand, also in this embodiment avoiding the use of an adhesive on the outer surface of the balloon or on the inner surface of the stent does allow for a reliable and smooth stent expansion.

In yet another embodiment, the invention is directed to a method for improving stent retention and foreshortening of a balloon catheter comprising a medical balloon and a second expandable medical device, desirably a stent. In this method, an inner layer of the medical balloon which is expandable and contractible through pressure provided by a gas and/or a liquid to its inner surface and desirably is having a lower compliance rate and/or higher burst pressure and/or higher durometer than the outer layer is provided. In addition, also an outer layer of the medical balloon is provided whose outer surface has a higher adhesion strength in contact to the second expandable medical device, than the inner layer, and also is not formed by an adhesive.

In yet another embodiment, the invention is directed to a method for improving stent retention and foreshortening of a balloon catheter comprising a medical balloon and a second expandable medical device, desirably a stent. In this method, an inner layer of the medical balloon which is expandable and contractible is provided as well as an outer layer of the medical balloon whose outer surface is uneven and is having a considerably higher adhesion strength when trying to fix the second expandable medical device, (the stent) than the inner layer, but which is not formed by an adhesive. The uneven surface of the outer layer is provided either by disposing the outer layer in such a way on the inner layer that inter-spaces, hollow areas between the outer layer and the inner layer, are formed or by folding the outer layer (providing access material) in many folds so that as a result in some places a part of the outer surface of the outer layer is facing another part of the outer surface of the outer layer, so getting in contact with each other.

In a further embodiment, the invention is directed to a method of producing a medical device according to the invention. In this method, the inner layer and the outer layer are either co-extruded or consecutively extruded or the outer layer is formed first, preferably by extrusion, and then the outer layer is layered, laminated or extruded onto the outer surface of the inner layer.

In another further embodiment, the invention is directed to a method of producing a certain embodiment of the medical device according to the invention. In this method, the uneven outer layer is formed either by disposing the outer layer in such a way on the inner layer that inter-spaces, hollow areas between the outer layer and the inner layer, are formed or by folding the outer layer (providing access material) in many folds so that as a result in some places a part of the outer surface of the outer layer is facing another part of the outer surface of the outer layer, so getting in contact with each other In a further embodiment, the invention is directed to a method of treatment of a disease, like a vascular disease, especially a stenosis, using in a patient, being a mammal, especially a human, in need thereof a medical device according to the invention, desirably in minimal invasive surgery like PTCA.

In yet another embodiment, the invention is directed to the use of a medical device according to the invention for the treatment of a disease, like a cardiovascular disease, especially a stenosis, especially through minimal invasive surgery like PTCA.

These and other objects and features of the present invention will become more fully apparent from the following description and appended claims, or may be learned by the practice of the invention as set forth hereinafter.

BRIEF DESCRIPTION OF THE DRAWINGS

FIG. 5 depicts—in a slightly abstracted form—an embodiment as already described and shown in FIG. 1. The difference rests in that the outer layer (5) is not disposed over the whole of the outer surface (7a) of inner layer (4) but is limited to the area (A) designated to carry the stent (2, not shown). In addition, the outer layer (5) is disposed in a wavy pattern.

DETAILED DESCRIPTION OF THE INVENTION

While the invention may be embodied in many different forms, there are described in detail herein specific preferred embodiments of the invention. This description is an exemplification of the principles of the invention and is not intended to limit the invention to the particular embodiments illustrated.

Figure 1:
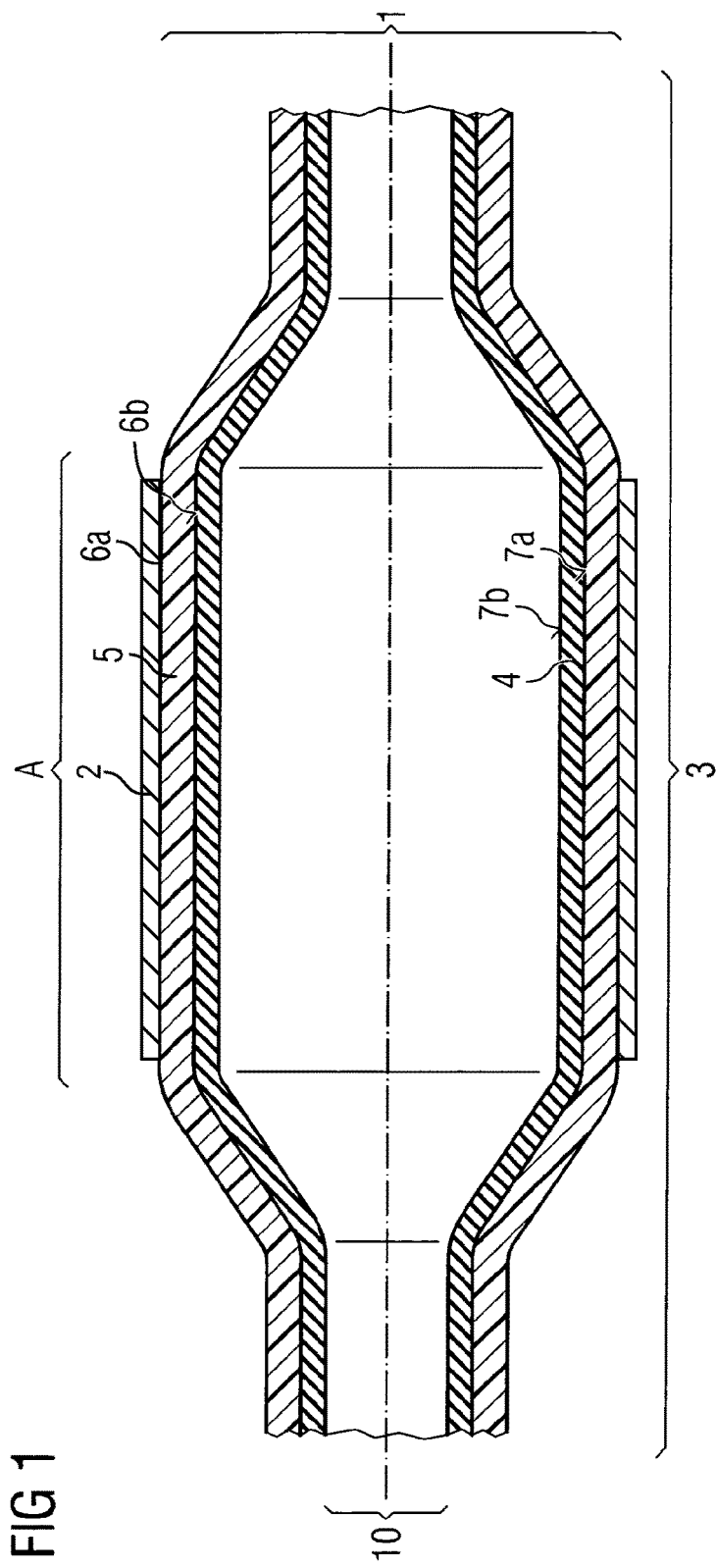
FIG. 1 depicts an embodiment of the invention showing a medical device (1) in form of a balloon catheter for delivering a second expandable medical device (2) (stent). The expandable and contractible device (3), the medical balloon, is constructed out of 2 layers, an inner layer (4) and an outer layer (5). The inner layer (4) is fixed air-tightly to the catheter shaft (10, not shown) to allow its expansion and contraction through the application of different levels of pressure provided by a gas and/or a liquid to its inner surface (7b). Area A is shown to identify the area designated to carry the stent (2). Over the whole of its outer surface (7a) is disposed the outer layer (5).

In one embodiment, as depicted in FIG. 1, the instant invention is directed to a medical device (1) comprising an expandable and contractible member (3), comprising an inner layer (4) and an outer layer (5), and a second expandable medical device (2). The inner layer is expandable and contractible through pressure provided by a gas and/or a liquid to its inner surface. It also desirably has a lower compliance rate and/or higher burst pressure and/or higher durometer than the outer layer, thus transferring stability to the expandable and contractible member (3). Most of the time thus, the inner layer (4) is air-tightly bound to another surface (e.g., a shaft) in the medical device (1), thus allowing its inflation/expansion. Desirably, the inner layer consists of polymeric material of low compliance and high burst-pressure as PEBAX®, like PEBAX® of a shore hardness of more than 40D, preferably more than 55 D, or Nylon—like Nylon 12—or mixtures thereof. On the other hand, the outer surface (6a) of the outer layer (5) does have a higher adhesion strength, i.e., a lower durometer in contact to the second expandable medical device (2), than the inner layer (4), and is not formed by an adhesive. Desirably, the outer layer (5) does not consist of an adhesive; preferably does not comprise an adhesive. By choosing a surface of high adhesion strength the grip or adhesion force, i.e., the friction between the surface of the balloon and the stent (or graft, etc.) is improved, to help in better stent retention and especially avoiding the longitudinal slip of the stent during expansion of the balloon and thus avoiding longitudinally compression of the stent by the increasing balloon cones and thus minimizing foreshortening of the stent during expansion. On the other hand, avoiding the use of an adhesive on the outer surface of the balloon or on the inner surface of the stent does allow for a reliable and smooth stent expansion and consequent catheter removal.

An "adhesive", as defined in this application, is defined as a compound that adheres or bonds two items together, either being natural or synthetic and specifically encompasses glues, them being fluid adhesives. As defined here the term "adhesive" is exclusively meant to include compounds adhering adhesion through chemical means, especially by actual chemical bonds, electrostatic forces (like hydrogen bond), or through van der Waals forces. Especially included are pressure sensitive adhesives. Selected pressure sensitive adhesives include silicone type pressure sensitive adhesives, acrylic type pressure sensitive adhesives and urethane type pressure sensitive adhesives. Examples of acrylic type pressure sensitive adhesives include NeoTac A-580, NeoTac A-574, NeoTac 2010, NeoTac 2457, NeoTac 2465, NeoTac 5468 all from Zeneca Resins. An example of a urethane type pressure sensitive adhesive is NeoTac 560 (Zeneca Resins).

The term "Adhesion strength" on the other hand is defined as the force [N] that is needed to separate two items being adherent to one another (in the current case, e.g., stent and outer surface of outer layer) and this might be measured, e.g., by a wedge test, a peel test or a double cantilever beam test, or any other adhesion test known in the art.

The term "PEBA" (Polyether Block Amide) is a block co-polymer of a polyamide with a polyether comprising an alcoholic terminal group and is also (in the context of this application fully equivalently) known under its trade name "PEBAX".

Desirably, in the medical device (1) according to the invention, the expandable and contractible member (3) is a medical balloon and the medical device (1) is a balloon catheter. Also desirably the second expandable medical device (2) is a stent, a stent graft, a graft or a graft connector, preferably is a stent. Additional details concerning the construction of suitable stent delivery apparatuses for use in the invention may be found in U.S. Pat. Nos. 6,036,697, 5,893,868 and 5,957,930 and elsewhere in the patent literature. Any suitable stent may be used whether formed of metal or of polymeric material or of another material. Examples of suitable stents may be found in U.S. Pat. No. 6,033,433, U.S. Pat. Nos. 6,602,285, and 6,533,809. The Medical balloon is capable of being expanded and contracted.

As a general information and with the focus of this invention on balloon material for balloon catheters, one of the main parameters of a balloon is compliance, the change of the balloon diameter with rising inflation pressure; as used herein three categories are being identified:

Non-compliant (NC) with a diameter increase of up to 0.55% per bar;
Semi-compliant (SC) with a diameter increase of between 0.55 to 0.8% per bar; and/or
Compliant with a diameter increase over 0.8% per bar as the balloon is pressurized from an inflation pressure between the nominal pressure and rated burst pressure.

While a certain level of compliance is needed to allow the compression of the arterio-sclerotic plaque in a vessel, an amount of pressure expressed on the stenosis as executed by a more non-compliant balloon is also needed. Also semi-compliant and compliant balloons are more prone to failure during PTCA and also "dog-boning", an inflation of the balloon outside the stenotic area of the vessel resulting sometimes in devastating stress on the healthy part of the vessel.

Another main parameter of a balloon in a balloon catheter device is burst pressure, the pressure a balloon in a balloon catheter device can withstand from within before bursting. While a certain degree of pressure expressed on the stenosis is a clear necessity for the function of a balloon catheter device the risks set to this pressure by the obviously devastating results of a possible burst of the balloon while in a lumen, e.g., of a vessel, do considerably limit the options given to a practitioner in using this device. Thus, also a high resistance to burst pressure is mostly a wanted effect in the balloon of a balloon catheter device.

The terms "Balloon", "Medical Balloon" or "balloon material" in the context of this invention especially means a balloon like those used in coronary balloon angioplasty and the material used for these balloons, especially balloon catheters. In this, e.g., a balloon catheter is inserted into an artery or other lumen and advanced to, e.g., a narrowing in a coronary artery. The balloon is then inflated by gas or fluids to enlarge the lumen and/or—often—to place a medical device.

The term "Stent" means an elongate implant with a hollow interior and at least two orifices and usually a circular or elliptical, but also any other, cross section, preferably with a perforated, lattice-like structure that is implanted into vessels, in particular blood vessels, to restore and maintain the vessels patent and functional.

The term "Graft" means an elongate implant with a hollow interior and with at least two orifices and usually circular or elliptical, but also any other, a cross section and with at least one closed polymer surface which is homogeneous or, optionally, woven from various strands. The surface preferably is impermeable to corpuscular constituents of blood and/or for water, so that the implant serves as a vascular prosthesis and is usually employed for damaged vessels or in place of vessels.

The term "Stent graft" means a connection between a stent and a graft. A stent graft preferably comprises a vascular prosthesis reinforced with a stent (both as defined above), wherein a polymer layer is homogeneous or, optionally, woven, knitted plaited etc. from various strands and is either impermeable for corpuscular constituents of blood and/or for water or can also be permeable. More preferably, the stent has on at least 20% of its surface a perforated (lattice-like), preferably metallic, outer layer and at least one closed polymer layer that is located inside or outside the stent outer layer. The closed polymer layer may be homogeneous or, optionally, woven from various strands, and is impermeable for corpuscular constituents of blood and/or for water. Optionally, where the closed polymer layer is disposed inside the metallic outer layer, a further perforated (lattice-like), preferably metallic, inner layer may be located inside the polymer layer.

The term "Graft connector" means an implant that connects at least two hollow organs, vessels or grafts, consists of the materials defined for grafts or stent grafts and/or has the structure defined for the latter. Preferably, a graft connector has at least two, three or four, orifices, arranged, for example, as an asymmetric "T" shape.

The term "Catheter" means a tubular instrument intended for introduction into hollow organs. More preferably, a catheter may be designed for use in guiding other catheters, or for angiography, ultrasound imaging, or—especially—balloon catheters for dilatation or stent delivery. This includes also a "Catheter pump" meaning a catheter provided on its tip with a propeller able to assist the pumping of the myocardium.

Desirably, in the medical device (1) according to the invention
the inner layer (4) consists of more than one inner sub-layer; or
the outer layer (5) consists of more than one outer sub-layer; or
the inner layer (4) consists of more than one inner sub-layer and the outer layer (5) consists of more than one outer sub-layer.

Figure 3:
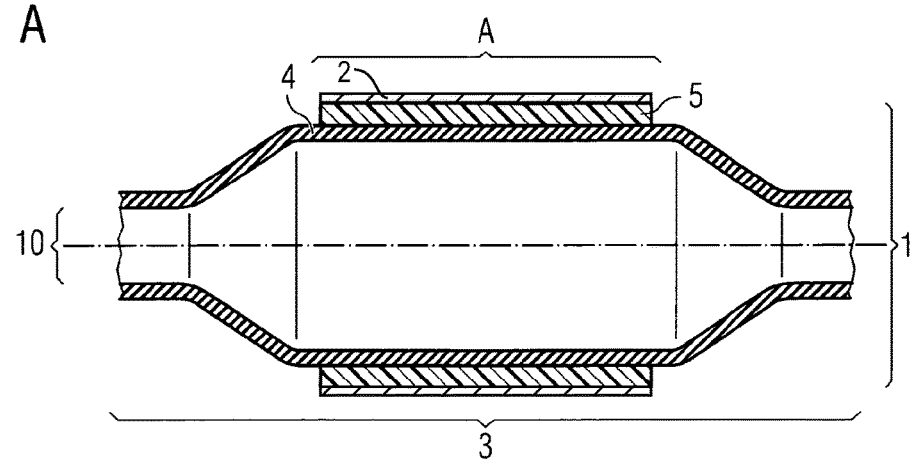
FIG. 3 depicts—in a slightly abstracted form and in 2 sub-pictures A) and B)—an embodiment as already described and shown in FIG. 1. The difference rests in that the outer layer (5) is not disposed over the whole of the outer surface (7a) of inner layer (4) but is limited to the area (A) designated to carry the stent (2). In addition, as can be seen in FIG. 3B) the outer layer (5) may be disposed in a criss-cross pattern.
Figure 3:
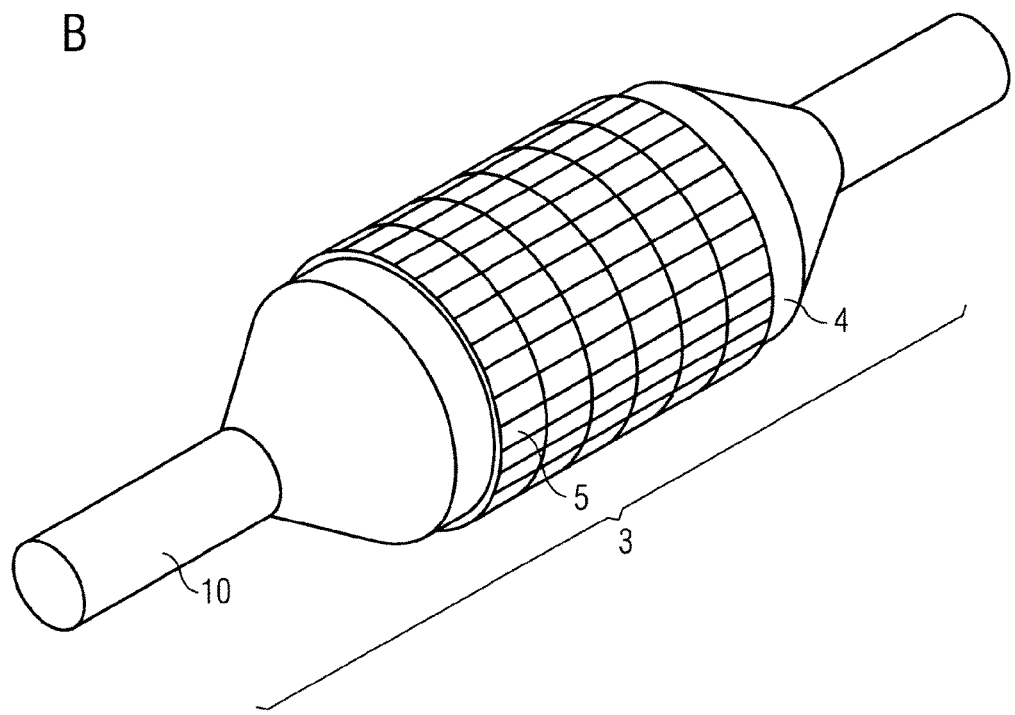

In a further embodiment of the medical device (1) according to the invention—as depicted in FIGS. 3 and 5—the outer layer (5) is only covering part of the outer surface (7a) of the inner layer (4), preferably is only covering the part of the outer surface (7a) of the inner layer (4), that is covered by the second expandable medical device (2). Thereby, the purpose of this invention is still served which aims at better stent retention on the outer surface of the medical balloon. In a further embodiment being related hereto in the medical device (1) according to the invention—as depicted in FIGS. 3 and 5—the outer layer (5) is arranged in a pattern, preferably is arranged in a pattern selected from orientations and shapes like circumferential, longitudinal, angular, or chaotic.

Also desirably, in one embodiment of the medical device (1) according to the invention the outer surface (6a) of the outer layer (5) consists of a Block-Copolymer, preferably consists of PEBA®; most preferably consists of a PEBA® of a shore hardness of equal to or less than 40D. Especially these materials provide a sticky/tacky surface giving good adhesion strength, but also all other suitable materials giving this sticky/tacky surface may be used.

In a further embodiment of the medical device (1) according to the invention:

(a) the outer layer (5) is comprising PEBA® or Nylon or mixtures thereof, preferably consists of PEBA® of a shore hardness of equal to or less than 40D;
or
(b) the outer layer (5) is comprising at least one outer sub-layer comprising PEBA® or Nylon or mixtures thereof, preferably at least one outer sub-layer consists of a PEBA® of a shore hardness of equal to or less than 40D.

Figure 2:
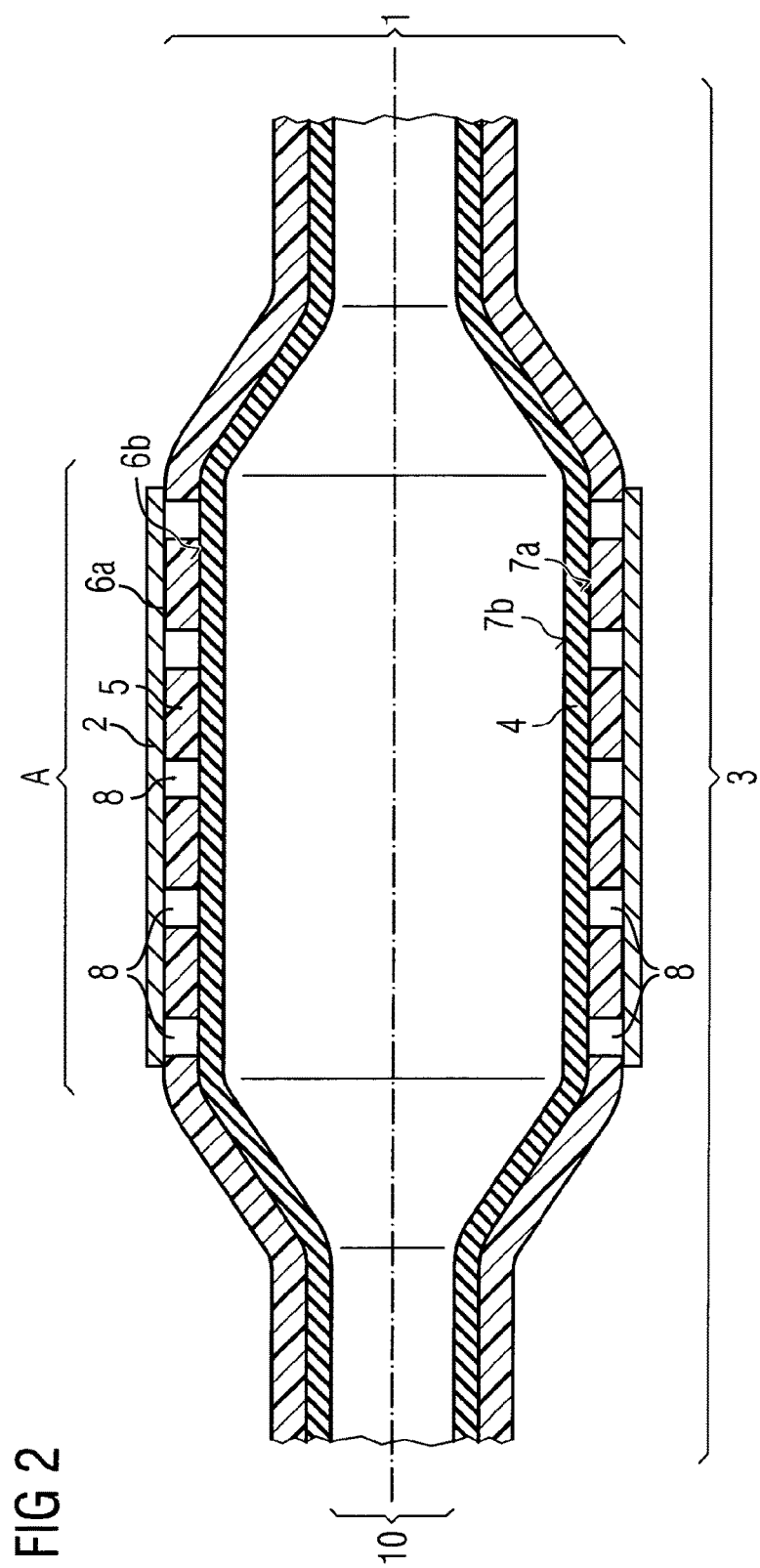
FIG. 2 depicts an embodiment of the invention showing a medical device (1) in form of a balloon catheter for delivering a second expandable medical device (2) (stent). The expandable and contractible device (3), the medical balloon, is constructed out of 2 layers, an inner layer (4) and an outer layer (5). The inner layer (4) is fixed air-tightly to the catheter shaft (10, not shown) to allow its expansion and contraction through the application of different levels of pressure provided by a gas and/or a liquid to its inner surface (7b). Area A is shown to identify the area designated to carry the stent (2). The outer surface (6a) of and the whole of outer layer (5) is perforated with holes (8).

In another embodiment, of the invention as depicted in FIG. 2, in the medical device (1) according to the invention the outer layer (5) comprises at least one outer sub-layer or outer surface (6a) being perforated by holes (8), preferably the complete outer layer (5) is being perforated by holes (8). These holes might especially be useful in increasing adhesion strength.

Figure 4:
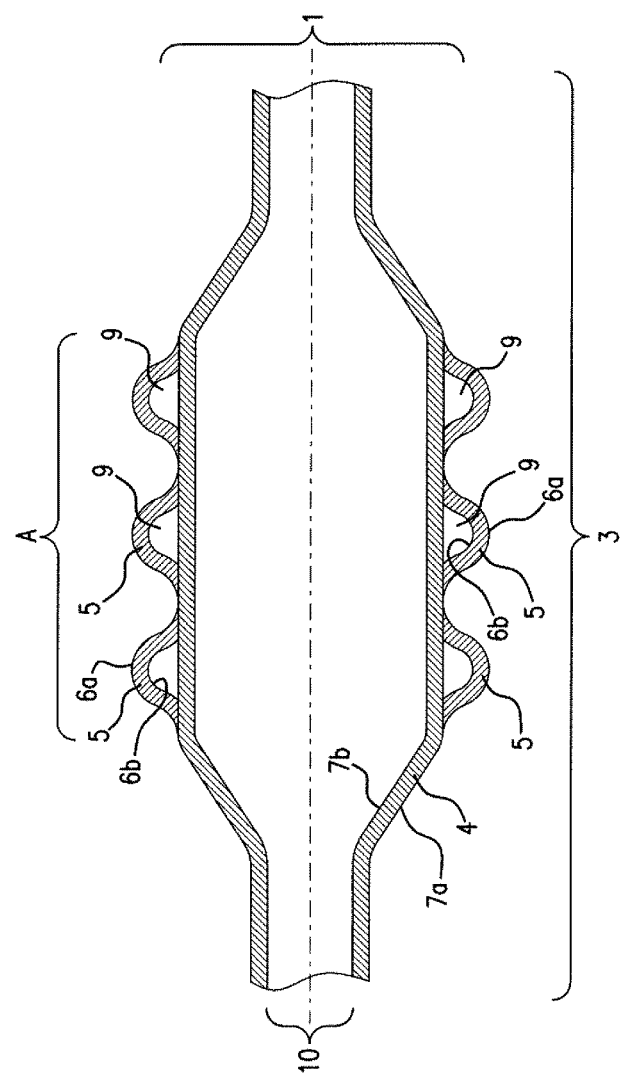
FIG. 4 depicts an embodiment of the invention showing a medical device (1) in form of a balloon catheter for delivering a second expandable medical device (2) (stent, not shown). The expandable and contractible device (3), the medical balloon, is constructed out of 2 layers, an inner layer (4) and an outer layer (5). The inner layer (4) is fixed air-tightly to the catheter shaft (10, not shown) to allow its expansion and contraction through the application of different levels of pressure provided by a gas and/or a liquid to its inner surface (7b). On its outer surface (7a) is disposed—only in the area (A) designated to carry the stent (2, not shown)—the outer layer (5). The outer layer is showing an uneven outer surface (6a) being arranged in form of "cushions". The arrangement of the outer layer (5) on the inner layer (4) led to the formation of various inter spaces (9) between the inner surface (6b) of outer layer (5) and outer surface (7a) of inner layer (4).

A further aspect of the invention—as depicted in FIG. 4 is drawn to a medical device (1) comprising an expandable and contractible member (3), comprising an inner layer (4) and an outer layer (5), and a second expandable medical device (2). The inner layer is expandable and contractible through pressure provided by a gas and/or a liquid to its inner surface. Desirably, the inner layer consists of polymeric material of low compliance and high burst-pressure such as for example and not limitation to PEBAX®, like PEBAX® of a shore hardness of more than 40D, preferably more than 55D, or Nylon—like Nylon 12—or mixtures thereof. On the other hand, the outer surface (6a) of the outer layer (5) does have a higher adhesion strength in contact to the second expandable medical device (2), than the inner layer (4), and is not formed by an adhesive. Desirably, the outer layer (5) does not consist of an adhesive; preferably does not comprise an adhesive. The outer layer (5) is forming an uneven outer surface (6a). This is desirably achieved by disposing the outer layer (5) on top of the outer surface (7a) of the inner layer (4) in a way to allow forming of at least one inter-space (9), hollow areas between the outer layer (5) and the outer surface (7a) of the inner layer (4). In another alternative this is achieved by folding the outer layer (5) (providing excess material) in many folds so that as a result in some places a part of the outer surface (6a) of the outer layer (5) is facing another part of the outer surface (6a) of the outer layer (5), so getting in contact ("face-to-face") with each other. Advantageously, this uneven outer surface (6a) overall increases adhesion of the outer layer (5) and thus of the medical balloon (3) to the second expandable medical device (2), the stent. Thus, it is improving on stent retention and foreshortening. On the other hand, avoiding the use of an adhesive also on the outer surface of the balloon or on the inner surface of the stent, does allow for a reliable and smooth stent expansion and consequent catheter removal. Preferably the outer layer (5) is only covering part of the outer surface (7a) of the inner layer (4), most preferably is only covering the part (area A) of the outer surface (7a) of the inner layer (4), that is covered by the second expandable medical device (2). Also desirably, the inner layer (4) and/or the outer layer (5) is/are consisting of PEBAX® or Nylon or mixtures thereof. Desirably, the outer layer (5) is arranged in a pattern, preferably is arranged in a pattern selected from orientations and shapes like circumferential, longitudinal, angular, or chaotic. Also preferably the at least one outer space (9) is filled with liquid or gas or is devoid of gas or liquids. The latter usually is achieved by applying a vacuum.

Preferably, the outer layer (5) is arranged in such a way as to cover only parts of area A (the area that is covered by the second expandable medical device (2)) of the outer surface (7a) of the inner layer (4), preferably covering less than 80%, less than 60%, less than 40%, less than 20% or less than 10% of the outer surface (7a) of the inner layer (4) in area A. As stated above, desirably the outer layer (5) is arranged in a pattern consisting of strips of the outer layer (5) covering the outer surface (7a) of the inner layer (4) in the pattern indicated. For clarification this means that according to the pattern, strips of the outer layer (5) are covering the outer surface (7a) of the inner layer (4) while other parts of the outer surface (7a) of the inner layer (4) are not covered by an outer layer (5). In a very preferred embodiment, the outer layer (5) is arranged in a pattern consisting of strips of the outer layer (5) covering the outer surface (7a) of the inner layer (4) in the pattern indicated, resulting in these strips of the outer layer (5) only covering parts of area A (the area that is covered by the second expandable medical device (2)) of the outer surface (7a) of the inner layer (4), preferably covering less than 80%, less than 60%, less than 40%, less than 20% or less than 10% of the outer surface (7a) of the inner layer (4) in area A. This arrangements in a pattern (of strips) (also possibly being called riffled) allows for a very good embedding of the second expandable medical device (2) (e.g., a stent) resulting in an improved stent retention during delivery. By the pattern, the outer surface of the expandable and contractible member (3) gets a certain kind of "grip" on the surface like a tyre profile where the areas uncovered by the outer layer (5) allow for the strips of the outer layer (5) to expand into them and thus flexibly attach to the second expandable medical device (2).

In an embodiment of the medical device (1) according to the invention with an uneven outer surface (6a) of outer layer (5) the expandable and contractible member (3) is a medical balloon and the medical device (1) is a balloon catheter. Also desirably the second expandable medical device (2) is a stent, a stent graft, a graft or a graft connector, preferably is a stent. Additional details concerning the construction of suitable stent delivery apparatuses for use in the invention may be found in U.S. Pat. Nos. 6,036,697, 5,893,868 and 5,957,930 and elsewhere in the patent literature. Any suitable stent may be used whether formed of metal or of polymeric material or of another material. Examples of suitable stents may be found in U.S. Pat. Nos. 6,033,433, 6,602,285, and 6,533,809. The Medical balloon is capable of being expanded and contracted.

A further aspect of the invention is drawn to a medical device (1) comprising an expandable and contractible member (3), comprising an inner layer (4) and an outer layer (5), and a second expandable medical device (2), wherein the outer layer (5) is forming an uneven outer surface (6a), either (a) by being disposed on top of the outer surface (7a) of the inner layer (4) in a way to allow forming of at least one inter-space (9) between the outer layer (5) and the outer surface (7a) of the inner layer (4); or (b) by being folded thus, so that at least one part of the outer surface (6a) of outer layer (5) is facing another part of the outer surface (6a) of outer layer (5). Advantageously, this uneven outer surface (6a) overall increases adhesion of the outer layer (5) and thus of the medical balloon (3) to the second expandable medical device (2), the stent. Thus it is improving on stent retention and foreshortening. Preferably the outer layer (5) is only covering part of the outer surface (7a) of the inner layer (4), most preferably is only covering the part (area A) of the outer surface (7a) of the inner layer (4), that is covered by the second expandable medical device (2). Also desirably the inner layer (4) and/or the outer layer (5) is/are consisting of PEBAX® or Nylon or mixtures thereof. Desirably, the outer layer (5) is arranged in a pattern, preferably is arranged in a pattern selected from orientations and shapes like circumferential, longitudinal, angular, or chaotic. Also preferably, the at least one outer space (9) is filled with liquid or gas or is devoid of gas or liquids. The later usually is achieved by applying a vacuum.

In yet another aspect and embodiment, the current invention is directed to a method for improving stent retention and reducing stent foreshortening of a balloon catheter (1) comprising a medical balloon (3) and a second expandable medical device (2), desirably a stent. In this method, an inner layer (4) of the medical balloon (3) which is expandable and contractible through pressure provided by a gas and/or a liquid to its inner surface (7b) and desirably has a lower compliance rate and/or higher burst pressure and/or higher durometer than the outer layer (5) is provided, thus transferring stability to the medical balloon (3). Desirably, the inner layer (4) consists of polymeric material of low compliance and high burst-pressure as PEBAX®, like PEBAX® of a shore hardness of more than 40D, preferably more than 55D, or Nylon—like Nylon 12—or mixtures thereof. In addition, also an outer layer (5) of the medical balloon (3) is provided whose outer surface (6a) is having a higher adhesion strength in contact to the second expandable medical device (2), than the inner layer (4), and also is not formed by an adhesive.

Desirably, in this method of improving stent retention the expandable and contractible member (3) is a medical balloon and the medical device (1) is a balloon catheter. Also desirably the second expandable medical device (2) is a stent, a stent graft, a graft or a graft connector, preferably is a stent. Additional details concerning the construction of suitable stent delivery apparatuses for use in the invention may be found in U.S. Pat. Nos. 6,036,697, 5,893,868 and 5,957,930 and elsewhere in the patent literature. Any suitable stent may be used whether formed of metal or of polymeric material or of another material. Examples of suitable stents may be found in U.S. Pat. Nos. 6,033,433, 6,602,285, and 6,533,809. The Medical balloon is capable of being expanded and contracted.

Also desirably, in another embodiment, of the method for improving stent retention in the medical device (1) according to the invention—as depicted in FIGS. 3 and 5—the outer layer (5) is only covering part of the outer surface (7a) of the inner layer (4), preferably is only covering the part of the outer surface (7a) of the inner layer (4), that is covered by the second expandable medical device (2). Thereby, the purpose of this invention is still served which aims at better stent retention on the outer surface of the medical balloon. In a further embodiment being related hereto in the medical device (1) according to the invention—as depicted in FIGS. 3 and 5—the outer layer (5) is arranged in a pattern, preferably is arranged in a pattern selected from orientations and shapes like circumferential, longitudinal, angular, or chaotic.

Also desirably, in yet a further embodiment of the method for improving stent retention in the medical device (1) according to the invention the outer surface (6a) of the outer layer (5) consists of a Block-Copolymer, preferably consists of PEBA®; most preferably consists of a PEBA® of a shore hardness of equal to or less than 40D. Especially these materials are providing a sticky/tacky surface giving good adhesion strength, but also all other suitable materials giving this sticky/tacky surface may be used.

Also desirably, in a further embodiment of the method for improving stent retention in the medical device (1) according to the invention (a) the outer layer (5) is comprising PEBA® or Nylon or mixtures thereof, preferably consists of PEBA® of a shore hardness of equal to or less than 40D;
or
(b) the outer layer (5) is comprising at least one outer sub-layer comprising PEBA® or Nylon or mixtures thereof, preferably at least one outer sub-layer consists of a PEBA® of a shore hardness of equal to or less than 40D.

In yet another embodiment—also of the method described above—the invention is directed to a method for improving stent retention and reduction of stent foreshortening of a balloon catheter (1) comprising a medical balloon (3) and a second expandable medical device (2), desirably a stent. In this method, an inner layer (4) of the medical balloon (3) which is expandable and contractible is provided as well as an outer layer (5) of the medical balloon (3) whose outer surface is uneven and is having a considerably higher adhesion strength when trying to fix the second expandable medical device (2), (the stent) than the inner layer (4), but which is not formed by an adhesive. The uneven outer surface (6a) of the outer layer (5) is provided either by disposing the outer layer (5) in such a way on the inner layer (4) that inter spaces (9), hollow areas between the outer layer and the inner layer, are formed or by folding the outer layer (5) (providing access material) in many folds so that as a result in some places a part of the outer surface (6a) of the outer layer (5) is facing another part of the outer surface (6a) of the outer layer (5), so getting in ("face-to-face") contact with each other.

Also desirably, in another embodiment, of the method for improving stent retention in the medical device (1) with an uneven outer surface (6a) according to the invention—as depicted in FIGS. 3 and 5—the outer layer (5) is only covering part of the outer surface (7a) of the inner layer (4), preferably is only covering the part of the outer surface (7a) of the inner layer (4), that is covered by the second expandable medical device (2). Thereby, the purpose of this invention is still served which aims at better stent retention on the outer surface of the medical balloon. In a further embodiment being related hereto in the medical device (1) according to the invention—as depicted in FIGS. 3 and 5—the outer layer (5) is arranged in a pattern, preferably is arranged in a pattern selected from orientations and shapes like circumferential, longitudinal, angular, or chaotic. Desirably, the at least one inter space (9) is filled with liquid or gas or is devoid of gas or liquids and/or the outer layer (5) and/or the inner layer (4) consists of PEBAX® or Nylon or mixtures thereof.

Another aspect and embodiment of the current invention is directed to a method of producing a medical device according to the invention. In this method, the inner layer (4) and the outer layer (5) are either co-extruded or consecutively extruded or the outer layer (4) is formed first, preferably by extrusion, and then the outer layer (5) is layered, laminated or extruded onto the outer surface (7a) of the inner layer (4), desirably being arranged in a pattern, e.g., a pattern selected from orientations and shapes like circumferential, longitudinal, angular, or chaotic. It is also desirably if at least one inter space (9) (desirably all inter spaces (9)) is/are filled with liquid or gas or is devoid of gas or liquids (which is achieved by applying a vacuum removing any remaining media). Desirably, the outer layer (5) consists of PEBAX® or Nylon or mixtures thereof.

Another aspect and embodiment of the current invention is directed to a method of producing a medical device according to the invention, wherein an uneven outer layer (5) is formed either by disposing the outer layer (5) in such a way on the inner layer (4) that inter-spaces (9), hollow areas between the outer layer (5) and the inner layer (4). In another variant the uneven outer layer (5) is formed by folding the outer layer (5) (providing access material) in a multitude of folds so that as a result in some places a part of the outer surface (6a) of the outer layer (5) is facing another part of the outer surface (6a) of the outer layer (5), so getting in contact (face-to-face) with each other. Desirably, the outer layer (5) is being arranged in a pattern, e.g., a pattern selected from orientations and shapes like circumferential, longitudinal, angular, or chaotic. Desirably, the outer layer (5) consists of PEBAX® or Nylon or mixtures thereof.

Another aspect and embodiment of the current invention is directed to a method of treatment of a disease, like a vascular disease or cardiovascular disease, especially a stenosis, using in a patient, being a mammal, especially a human, in need thereof a medical device (1) according to the invention, desirably in minimal invasive surgery like PTCA. In this, the first expandable and contractible member (3) (the Medical Balloon) comprising 2 layers with the outer layer (5) having a higher adhesion strength in contact the second expandable medical device (2), the stent, than the inner layer (4) is advantageously showing more stent retention and less stent foreshortening allowing a more precise placement of the stent, e.g., in PTCA.

A further aspect and embodiment of the current invention is directed to the use of a medical device (1) according to the invention for the treatment of a disease, like a vascular disease or cardiovascular disease, especially a stenosis, especially through minimal invasive surgery like PTCA. In this, the first expandable and contractible member (3) (the Medical Balloon) comprising 2 layers with the outer layer (5) having a higher adhesion strength in contact the second expandable medical device (2), the stent, than the inner layer (4) is advantageously showing more stent retention and less stent foreshortening allowing a more precise placement of the stent, e.g., in PTCA.

Example

Example 1: Balloon-Catheter for Delivery of a Stent with a Medical Balloon Having 2 Layers Over the Whole Surface of the Medical Balloon In a balloon catheter (1)—depicted in FIG. 1—for delivery of a stent (2), the medical balloon (3), is constructed out of 2 layers, an inner layer (4) with an inner surface (7b) and an outer surface (7a) as well as an outer layer (5) with an inner surface (6b) and an outer surface (6a). The inner layer (4) is fixed air-tightly to the catheter shaft (10). This inner layer (4) can thus be expanded and contracted during PTCA or other minimal invasive surgery through the application of pressure provided by a gas and/or a liquid to its inner surface (7b) as a consequence also expanding stent (2) disposed about the balloon (3) in Area (A). Inner layer (4) is manufactured from nylon 12 giving the compliance and burst-pressure needed. Over the whole of the outer surface (7a) of inner layer (4) the outer layer (5) is disposed. The outer layer (4) is constructed from low durometer PEBAX® which by itself provides a tacky and sticky surface opposed to the smooth nylon 12, thus causing a high adhesion force between the stent (2) and the outer surface (6a) of outer layer (5), thus allowing good stent retention and reducing stent foreshortening.

Example 2: Balloon-Catheter for Delivery of a Stent with a Medical Balloon Having 2 Layers Over the Whole Surface of the Medical Balloon—Showing Perforations in the Outer Layer Example 2 exemplifies a balloon catheter (1)—depicted in FIG. 2—very similar to the one already described in example 1 and thus also showing a medical balloon (3) being constructed of 2 layers, an inner layer (4) and an outer layer (5) with the inner layer (4) being expandable and contractible. Again the inner layer (4) is manufactured from nylon 12 giving the compliance and burst-pressure needed. In principle the outer layer (5) is disposed over the whole of the outer surface (7a) of inner layer (4) and is constructed from low durometer PEBAX® of a shore hardness equal to or less than 40D. In difference to example 1 in this example the outer layer (5) is perforated by holes (8) down to the outer surface (7a) of the inner layer (4). Accordingly, the outer surface (5) has a high adhesion strength helping in stent retention and reducing stent foreshortening.

Example 3: Balloon-Catheter for Delivery of a Stent with a Balloon Having 2 Layers with the Outer Layer Only Covering the Area of Stent Contact in a Criss-Cross Pattern Example 3 exemplifies a balloon catheter (1)—depicted in FIG. 3—very similar to the one already described in example 1 and thus also showing a medical balloon (3) being constructed of 2 layers, an inner layer (4) and an outer layer (5) with the inner layer (4) being expandable and contractible. Again the inner layer (4) is manufactured from nylon 12 giving the compliance and burst-pressure needed. The outer layer (5) is exclusively disposed in a criss-cross pattern in area (A) designated to carry the stent (2) thus only in the area getting into contact with the stent (2). As the outer layer (5) is also constructed from low durometer PEBAX® providing a tacky/sticky surface with high adhesion strength this is providing stent retention and reduces stent foreshortening.

Example 4: Balloon-Catheter for Delivery of a Stent with a Balloon Having 2 Layers with the Outer Layer Only Covering the Area of Stent Contact in a Wavy Pattern Example 4 exemplifies a balloon catheter (1)—depicted in FIG. 5—very similar to the one already described in example 1 and thus also showing a medical balloon (3) being constructed of 2 layers, an inner layer (4) and an outer layer (5) with the inner layer (4) being expandable and contractible. Again the inner layer (4) is manufactured from nylon 12 giving the compliance and burst-pressure needed. The outer layer (5) is exclusively disposed in a wavy pattern in area (A) designated to carry the stent (2—not shown) thus only in the area getting into contact with the stent (2—not shown). As the outer layer (5) is also constructed from low durometer PEBAX® providing a tacky/sticky surface with high adhesion strength this is providing stent retention and reduces stent foreshortening.

Example 5: Balloon-Catheter for Delivery of a Stent with a Balloon Having 2 Layers with the Outer Layer Showing a Cushion Design in the Area of Stent Contact Example 5 exemplifies a balloon catheter (1)—depicted in FIG. 4—for delivery of a stent (2) with the medical balloon (3) being constructed from 2 layers. The inner layer (4) is fixed air-tightly to the catheter shaft (10). This inner layer (4) can thus be expanded and contracted during PTCA or other minimal invasive surgery through the application of pressure provided by a gas and/or a liquid to its inner surface (7b) as a consequence also expanding stent (2) disposed about the balloon (3) in Area (A). Inner layer (4) is manufactured either from nylon 12 or high durometer PEBAX® giving the compliance and burst-pressure needed. The outer layer (5) is showing an excess of material and is disposed on outer surface (7a) of inner layer (4), but only in the area (A) designated to carry the stent (2). The outer layer is showing an uneven outer surface (6a) being arranged in form of "cushions". The outer layer (4) is also manufactured from nylon 12 or high durometer PEBAX®. The arrangement of the outer layer (5) on the inner layer (4) led to the formation of various inter spaces (9) between the inner surface (6b) of outer layer (5) and outer surface (7a) of inner layer (4). These interspaces are either filled with liquids or gas or be evacuated. The uneven arrangement of the outer surface (6a) of outer layer (5) provides in itself a high adhesion strength in contact to the stent thus allowing also the smooth nylon 12 to be used as material for the outer layer (5), without stopping good stent retention or the reduction of stent foreshortening.

Example 6: Balloon-Catheter for Delivery of a Stent with a Balloon Having 2 Layers with the Outer Layer being Folded in the Area of Stent Contact Example 6 exemplifies a balloon catheter (1) very closely related to that already described in example 5. Opposed to example 5 the excess of material of outer layer (5) is folded on outer surface (7a) of inner layer (4), in the area (A) designated to carry the stent (2). The outer layer is showing an uneven outer surface (6a) as it is forming in certain areas a multitude of folds (double or triple layers) with parts of its outer surface (6a) coming into "face-to-face" contact with each other. The uneven arrangement of the outer surface (6a) of outer layer (5) provides in itself a high adhesion strength in contact to the stent thus allowing also, e.g., the smooth nylon 12 to be used as material for the outer layer (5), without stopping good stent retention or the reduction of stent foreshortening.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A balloon catheter comprising:
    a balloon having an inner layer and an outer layer, the inner layer defining an inner chamber and being expandable upon pressurization of the inner chamber, the outer layer disposed over an outer surface of the inner layer to define a plurality of discrete inter-space, hollow areas between an inner surface of the outer layer and the outer surface of the inner layer and spaced along a longitudinal length of the balloon, the outer layer having an uneven outer surface arranged in the form of cushions due to the plurality of discrete inter-space, hollow areas; and
    an expandable medical device mounted on the balloon in contact with the outer surface of the outer layer.
2. The balloon catheter of claim 1, wherein the outer layer comprises a higher adhesion strength than the inner layer.
3. The balloon catheter of claim 1, wherein the outer layer does not comprise an adhesive.
4. The balloon catheter of claim 1, wherein the inner layer has a higher Shore durometer hardness than the outer layer.
5. The balloon catheter of claim 1, wherein the inner layer comprises a polymer selected from the group consisting of polyether block amide, nylon and combinations thereof.
6. The balloon catheter of claim 5, wherein the polymer has a Shore hardness of more than about 40D.
7. The balloon catheter of claim 1, wherein the outer layer comprises polyether block amide.
8. The balloon catheter of claim 7, wherein the polyether block amide has a Shore hardness of equal to or less than about 40D.
9. The balloon catheter of claim 1, wherein the plurality of inter-space, hollow areas are filled with a fluid.
10. The balloon catheter of claim 1, wherein the plurality of inter-space, hollow areas are devoid of fluid.
11. The balloon catheter of claim 1, wherein the outer layer covers only a portion of the outer surface of the inner layer.
12. The balloon catheter of claim 11, wherein the outer layer covers the outer surface of the inner layer in a wavy pattern when viewed in longitudinal cross-section.
13. The balloon catheter of claim 1, wherein the outer layer is arranged in a pattern selected from the group consisting of circumferential, longitudinal, angular, chaotic, and combinations thereof.
14. The balloon catheter of claim 1, wherein the outer layer comprises at least one outer sub-layer having an outer surface perforated by holes.
15. The balloon catheter of claim 1, wherein the expandable medical device is selected from the group consisting of a stent, a stent graft, a graft, a graft connector, and combinations thereof.

* * * * *